(12) United States Patent
Gref et al.

(10) Patent No.: US 7,682,635 B2
(45) Date of Patent: Mar. 23, 2010

(54) AQUEOUS DISPERSIONS OF NANOMETRIC OR MICROMETRIC PARTICLES FOR ENCAPSULATING CHEMICAL COMPOUNDS

(75) Inventors: Ruxandra Gref, Chateanay Malabry (FR); Catherine Amiel, L'Hay les Roses (FR); Bernard Sebille, Clamart (FR); Patrick Couvreur, Villebon sur Yvette (FR)

(73) Assignees: Centre National de la Recherche Scientifique (C.N.R.S.), Paris (FR); Universite de Paris 11 - Paris SUD, Orsay (FR)

( * ) Notice: Subject to any disclaimer, the term of this patent is extended or adjusted under 35 U.S.C. 154(b) by 1146 days.

(21) Appl. No.: 10/520,657

(22) PCT Filed: Jul. 1, 2003

(86) PCT No.: PCT/FR03/02045

§ 371 (c)(1),
(2), (4) Date: Jun. 30, 2005

(87) PCT Pub. No.: WO2004/006897

PCT Pub. Date: Jan. 22, 2004

(65) Prior Publication Data

US 2005/0250881 A1 Nov. 10, 2005

(30) Foreign Application Priority Data

Jul. 11, 2002 (FR) .................................. 02 08766

(51) Int. Cl.
*A61K 9/50* (2006.01)
(52) U.S. Cl. ..................................................... 424/499

(58) Field of Classification Search ....................... None
See application file for complete search history.

(56) References Cited

U.S. PATENT DOCUMENTS 6,048,736 A * 4/2000 Kosak ......................... 436/536

FOREIGN PATENT DOCUMENTS

WO WO 00/01734 1/2000
WO WO 01/37665 A1 5/2001

OTHER PUBLICATIONS

McCormick et al.; Stimuli-Responsive Water Soluble and Amphiphilic Polymers—ACS Symposium Series; Chapter 4; Amiel et al.; "Macromolecular Assemblies Generated by Inclusion Complexes between Amphiphilic Polymers and β-Cyclodextrin Polymers in Aqueous Media" (2001).*

* cited by examiner

*Primary Examiner*—Robert A Wax
*Assistant Examiner*—Jeffrey T Palenik
(74) *Attorney, Agent, or Firm*—Stites & Harbison PLLC; Stephen J. Weyer; B. Aaron Schulman (57) ABSTRACT

A composition comprises an aqueous dispersion of particles (p) of mean hydrodynamic diameter between 50 and 5000 nm. The particles contain (A) polymers based on cyclodextrin units, comprising on average at least four cyclodextrin units within their structure; and (B) macromolecules of polysaccharides comprising groups G capable of forming inclusion complexes with the cyclodextrins present in the structure of the polymers (A), with an average number of groups G per polysaccharide macromolecule at least equal to three. The compounds (A) and (B) are water-soluble in the isolated state. A method is also provided which relates to the preparation of these compositions, as well as their use in order to achieve the encapsulation of compounds such as active substances.

24 Claims, 1 Drawing Sheet

AQUEOUS DISPERSIONS OF NANOMETRIC OR MICROMETRIC PARTICLES FOR ENCAPSULATING CHEMICAL COMPOUNDS

The present invention relates to aqueous dispersions of nanometer or micrometer dimensions, suitable for the encapsulation of chemical compounds and especially useful for carrying out the vectorisation of active substances at the level of cells or of target tissues, especially in pharmaceutical or cosmetic applications.

In the course of the last twenty years, numerous systems for vectorisation of active substances have been developed. In a general manner, the principle of vectorisation consists of trapping an active substance within a particle of micrometric or submicrometric size which can be administered in a subject to be treated (particularly by injection or ingestion) and by choosing the said particle in such a manner that it releases the active substance within a cell or a targeted tissue.

Within this context, development has been carried out in particular on the encapsulation of active substances by liposomes (lipid bilayers surrounding an aqueous core) or even by nanocapsules (polymer shells of sub-micrometer size containing a phase, generally oily, including the active substance).

More specifically, systems such as nanospheres or microspheres have also been developed, namely particles based on biocompatible and biodegradable polymers (for example polylactic acid or polycaprolactone) playing the role of a matrix capable of immobilising active substances and releasing them progressively within an organism where this system of encapsulation is introduced.

These systems of the nanosphere or microsphere type generally have a quite good capacity for vectorisation of active substances. However, these vectors of active substances currently have a major drawback. As a matter of fact, the processes of preparation of systems of this type which are currently known implement intermediate steps which generally imply the use of organic solvents or non-biocompatible surfactants which have to be eliminated. The elimination of these solvents and/or surfactants is generally long and expensive (carrying out dialysis, ultracentrifugation, . . . ), and it is rarely complete. Therefore, at the end of such purification steps trace amounts of solvents and/or surfactants generally remain, which is likely to create problems in terms of toxicity (for example if the solvent remaining in the state of traces is a solvent such as dichloromethane) and/or to degrade the active substances immobilised in the particles (traces of organic solvents can be for example denature fragile molecules of the peptide or protein type).

Now, the inventors have unexpectedly discovered that it is possible to produce aqueous dispersions of particles of nanosphere or microsphere type, suitable for vectorisation of active substances, without having to use organic solvents or surfactants in this connection.

More precisely, the inventors have discovered that, if one makes in aqueous medium a mixture of specific water-soluble compounds, namely (1) polymers comprising cross-linked cyclodextrin units and (2) macromolecules carrying groups able to form inclusion complexes with the cyclodextrins (such as, for example, polysaccharides substituted by aliphatic chains), one may observe under specific conditions, the spontaneous formation of a dispersion of particles of mean hydrodynamic diameter between 50 and 5000 nm, if subject to suitable choice of the used compounds (1) and (2) used.

Associations of polymers comprising cyclodextrin units and polysaccharides substituted by aliphatic chains in an aqueous medium have already been described. In this connection, it is especially known that, when polymers comprising cyclodextrin units and polysaccharides substituted by aliphatic chains are present in an aqueous medium, the formation of inclusion complexes between the aliphatic chains of the substituted polysaccharides and the cyclodextrin units of the polymers occurs, which leads to an association of the polymers and the polysaccharides.

However, until now, this association in an aqueous medium has always been specifically described as being capable of leading only to the formation of two types of associative systems, namely:

(I) a homogeneous single-phase comprising associated polymers and polysaccharides dissolved in the aqueous medium; or (II) a non-emulsifiable two-phase system comprising a first phase which is rich in polymers, dense and viscous (a so-called "gel") and a second homogeneous phase which is less dense and viscous (a so-called "supernatant") which is obtained by a mechanism known as "associative phase separation" which has in particular been described in a publication by the ACS, edited by C. McCormick (*Symposium Series*, No. 780, chapter 4, "*Stimuli-Responsive Water-Soluble and Amphiphatic Polymers*", C. Amiel et al, 2000).

In this connection, it is also known that certain associations (polymers comprising cyclodextrin units/polysaccharides substituted by aliphatic chains) lead, in an aqueous medium, exclusively to the formation of a system of type (I) regardless of the respective concentrations of polymers and polysaccharides (associations known here as type $a_I$). The type (II) system can only be obtained for other particular associations, known here as type $a_{II}$. In the following description, these specific associations of $a_{II}$ type will be designated by the generic term of auto-associative system "of a type which can lead, under certain concentration conditions, to an associative phase separation".

As regards the associations of type $a_{II}$ defined above, it should be emphasised that the associative phase separation can only be observed under specific concentration conditions, corresponding to a relatively limited range on a ternary water/polymer/polysaccharide diagram. It has hitherto been generally acknowledged that, in this range of specific concentrations, it was only possible to observe phenomena of the associative phase separation type leading to the formation of a system of type (II) and that, outside this range, it was only possible to observe the formation of a system of type (I).

The present invention is based on the entirely unexpected discovery of the possibility of forming a third type of system when starting from associations of type $a_{II}$. As regards these specific associations, the work of the inventors has actually allowed to evidence that a specific range of concentrations exists wherein a direct mixture of water, polymers based on cyclodextrin units, and polysaccharide grafted with aliphatic chains, leads to the formation of a dispersion of particles based on associated polymers and polysaccharides, having a mean hydrodynamic diameter at least equal to 50 nm, and most often having very good stability. More generally, the inventors have discovered that such dispersions of particles can be obtained by the direct mixture of water, polymers based on cyclodextrin units and macromolecules carrying groups likely to form inclusion complexes with the cyclodextrins.

In this connection, the inventors have established that the dispersion thus produced constitutes a metastable system, and that only the systems of type (I) and (II) are thermodynamically stable systems. Thus, if a dispersion as discovered by the inventors is subjected to sufficiently substantial shear conditions, a development towards a system of type (II) is generally observed. In this context, the inventors have however surprisingly discovered that the stability of the metastable dispersion produced is unexpectedly high, which especially makes it possible to contemplate its storage, dilution, or even its integration in complex compositions, for example in pharmaceutical or cosmetic compositions.

On the basis of the inventors' work, it has also been evidenced that the particles formed within the obtained metastable dispersions are especially suitable for the encapsulation of chemical compounds, and particularly for the vectorisation of active substances, with an effective and quantitative integration of the chemical compounds. In this scope, the inventors have especially evidenced that these particles allow to achieve a release of the active substances in a much more controlled manner than when using most of particles of nanosphere or microsphere type of the prior art, for which an immediate release of a significant fraction of the encapsulated active substances is generally observed after administration.

On the basis of these discoveries, the instant invention aims at providing new composition of particles of nanometric or micrometric dimensions, which allows easy encapsulation of chemical compounds, and especially of active substances.

Another object of the invention is to provide compositions comprising particles having no traces of organic solvent and surfactants, which may advantageously be substituted to the particles known from the prior art in the vectorisation of active substances. Within this context, an object of the invention is especially to provide compositions which make it possible to achieve a controlled release of active substances.

Another object of the invention is to provide compositions intended to administer active substances by ensuring "surreptitious (furtive) activity" in the organism, that is to say a capacity to circulate in a prolonged manner in the organism, particularly in the blood system, avoiding recognition by the immune system.

It is also an object of the invention to provide dispersions of particles free from surfactants and having nevertheless sufficient stability to be stored for a duration of about at least several days.

Thus, according to a first aspect, the present invention relates to a composition comprising an aqueous dispersion of particles (p) of mean hydrodynamic diameter between 50 and 5000 nm, wherein said particles contain in association:

(A) polymers based on cyclodextrin units, with an average content of at least 4 cyclodextrin units within their structure; and (B) macromolecules of polysaccharides comprising groups G capable of forming inclusion complexes with the cyclodextrins present in the structure of the said polymers (A), with an average number of groups G per polysaccharide macromolecule at least equal to 3, wherein said compounds (A) and (B) are water-soluble in the isolated state, i.e. preferably having a solubility at least equal to 1 g/l, and advantageously at least equal to 3 g/l, at 25° C.

The term "Composition comprising an aqueous dispersion of particles" is understood, within the context of the present invention, to mean a composition containing an aqueous medium (for example water, physiological serum or, more generally, an aqueous solution comprising one or several solutes (especially one or several salt(s) and/or sugar(s) such as sucrose or glucose for example) at concentrations preferably less than or equal to 20 g/l; or a mixture of the water/ alcohol type), wherein said particles are dispersed, these particles preferably being individual and advantageously having a rate of agglomeration below 80%, preferably below 50%, and preferably at most equal to 10% by number. A composition according to the invention advantageously essentially consists in a dispersion of the particles (p) in water, in an aqueous solution of glucose (in particular a glucose solution at a concentration of the order of 5% by mass), or even in an injectable solution, at physiological pH, e.g. in physiological serum. However, a composition according to the invention can also be a more complex composition, for example a composition such as a single or multiple emulsion, where the aqueous dispersion of the particles according to the invention acts as a continuous phase or a disperse phase. A composition according to the invention can also comprise, in addition to the particles based on the association of polymers (A) and (B), other particles of a mineral or organic nature.

The term "mean hydrodynamic diameter", in the sense of the present description, designates the size of a particle within an aqueous medium, which takes into account the average diameter of the particle in its conformation in the aqueous medium, as well as its possible solvation layer. The mean hydrodynamic diameter of a population of particles within an aqueous medium may especially be determined by quasi-elastic scattering of light within the medium under consideration, particularly by an apparatus of the Nanosizer type. This type of apparatus also allows to determine for the population of particles a polydispersity index of the hydrodynamic diameter, which indicates the distribution of the hydrodynamic diameters which is more or less narrow around the mean value.

Preferably within a composition according to the invention the mean hydrodynamic diameter of the particles (p) is greater than or equal to 80 nm, and it is advantageously at least equal to 100 nm. The particles (p) may have, for certain applications, a mean hydrodynamic diameter of between 1 and 5 microns (preferably less than 3 microns, if need be), but it is generally preferred for the mean hydrodynamic diameter of the particles (p) to be less than or equal to 500 nm. More preferably, the mean hydrodynamic diameter of the particles (p) is less than or equal to 400 nm, and advantageously less than or equal to 300 nm. Thus, in a particularly advantageous manner, the mean hydrodynamic diameter of the particles (p) is between 100 and 300 nm, and even more advantageously between 150 and 250 nm. Moreover, in a composition according to the invention the particles (p) are generally of substantially spherical morphology, and the index of polydispersity of the hydrodynamic diameter thereof, as measured with the aid of an apparatus of the Nanosizer type, is generally between 0.1 and 0.3, and it is advantageously less than 0.2.

The compounds (A) and (B) present in association within particles according to the invention are compounds which form, in an aqueous medium, an associative system (A+B) of the type of associations all previously defined, namely an associative system (A+B) of a type capable of leading, under certain concentration conditions, to an associative phase separation.

Thus the useful compounds (A) and (B) according to the invention are, in general, compounds such that a mixture of two aqueous solutions of these compounds at a concentration of 50 g/l in a proportion ranging from 1:5 to 5:1 by volume leads to the formation of a two-phase system of type (II) as defined previously.

The skilled person can easily check that candidate compounds (A) and (B) are actually capable of forming such a two-phase system by simple mixture of the aqueous solutions at ambient temperature. In order to select a candidate of type (A) it is preferable to mix a solution of this compound with a solution of a compound (B) as described below in the examples and, likewise, for a candidate of type (B) to make the mixture with a solution of a compound (A) as described below in the examples. In general, potential candidates can be tested with complementary compounds which have demonstrated their capacity for forming a system of type (II).

Preferably the compounds (A) and (B) present in a composition according to the invention are compounds such that a mixture of two aqueous solutions of these compounds at concentrations ranging from 1 g/l to 10 g/l, in a proportion ranging from 1:9 to 9:1 by volume, leads to the formation of particles of mean hydrodynamic diameter greater than 50 nm and less than 5000 nm.

These mixtures are extremely easy to produce, and it is sufficient then to check, by one of the conventional methods of analysis mentioned here, the appearance of the particles according to the invention.

The aqueous dispersion of particles (p) present within a composition according to the invention characteristically constitutes a metastable system. Consequently, if a composition according to the invention is subjected to a sufficient shear stress (typically centrifugation at a rate of at least 3000 r.p.m. for at least 20 minutes), an irreversible evolution of the dispersion towards a system of type (II) as defined previously is generally observed. Nevertheless, it should be noted that, despite its metastable character, the aqueous dispersion of particles (p) present within a composition according to the invention generally has substantial stability.

The stability of the particles (p) in aqueous dispersion can especially be demonstrated by the retention of the mean hydrodynamic diameter of the particles (p) following storage. Thus, in general, after a storage of 24 hours, the mean hydrodynamic diameter of the particles (p) of a composition according to the invention remains less than or equal to 5000 nm. In most cases, following storage for 24 hours, the mean hydrodynamic diameter of the particles (p) of a composition according to the invention remains less than or equal to 400 nm, preferably less than or equal to 350 nm, and even more advantageously less than or equal to 200 nm. Preferably the mean hydrodynamic diameter of the particles (p) remains less than or equal to 400 nm, and preferably less than or equal to 300 nm, following storage for 2 days, or indeed following storage for 5 days, and even in certain cases after storage for 15 days. However, it should be emphasised that in order to observe good retention of the mean hydrodynamic diameter of the particles (p) following prolonged storage it may sometimes be necessary to keep the composition in an non-oxidising atmosphere (for example under argon) so as to avoid ageing of the compounds (A) and/or (B), which is likely to call into question the stability of the metastable system formed.

The polymers (A) based on cyclodextrin units are essential constituents of the particles (p) present in dispersion in the composition according to the invention. These polymers (A) include on average at least 4 cyclodextrin units, preferably at least 9 cyclodextrin units, and advantageously at least 15 cyclodextrin units. In a particularly advantageous manner, it is preferable for the polymers (A) to comprise on average at least 100 cyclodextrin units, and advantageously at least 200 cyclodextrin units. Typically, the polymers (A) comprise on average at least 400 cyclodextrin units. The average number of cyclodextrin units present in the polymers (A) of a composition according to the invention may be example be established by steric exclusion chromatography and by nuclear magnetic resonance.

The cyclodextrin units present within the polymers (A) can, in general, be α-cyclodextrins, β-cyclodextrins, γ-cyclodextrins, or mixtures of at least two of these types of cyclodextrins. Nevertheless, the cyclodextrin units present in the polymers (A) preferably comprise β-cyclodextrins. In a particularly advantageous manner, all the cyclodextrin units present in the polymers (A) are β-cyclodextrins. According to a particular variant, the cyclodextrin units present in the polymers (A) are a mixture of β-cyclodextrins and α-cyclodextrins. According to this variant, it is generally preferred that the α-cyclodextrins represent less than 50%, and preferably less than 30% of the cyclodextrins present.

Within the polymers (A), the cyclodextrin units are generally linked to one another by hydrocarbon chains, linear or branched, which may be interrupted by one or several oxygen atoms, and as these chains are preferably alkyl, alkenyl or alkynyl chains, or also polyether chains, these chains may be substituted by hydrophilic groups (hydroxy groups for example). The chains linking the cyclodextrin units to one another have at least 3 carbon atoms and preferably from 4 to 50 carbon atoms, the shortest path between two cyclodextrin units being preferably constituted by a chain having between 3 and 8 carbon atoms. Advantageously the hydrocarbon chains linking two cyclodextrin units to one another within a polymer (A) satisfy the general formula, a group of formula —O—(—CH$_2$—CHOR$^{(n)}$—CH$_2$)—O—, where n is an integer between 1 and 50 (generally between 2 and 10) and where, in each of the n units (—CH$_2$—CHOR—CH$_2$), R$^{(n)}$ designates either a hydrogen atom or a —CH$_2$—CHOH—CH$_2$—O— chain linked to a cyclodextrin unit of the polymer.

Thus, the polymers (A) may typically be obtained by a polycondensation of cyclodextrin and epichlorhydrin molecules in a basic medium (generally in an aqueous medium with soda added, at a concentration by mass of 10 to 40%), the molar ratio cyclodextrins/epichlorhydrin being preferably between 1:15 and 1:1, and advantageously between 1:15 and 1:8. For further details concerning this synthesis and control of the mean number of cyclodextrin units integrated within the polymers (A) obtained according to this process, reference may be made in particular to the article by E. Renard et al, published in the *European Polymer Journal, vol.* 33, No 1, pp 49-57 (1997).

Regardless of the exact nature of the hydrocarbon chains linking the cyclodextrin units to one another, it is generally preferred that the total mass of the cyclodextrin units present within the polymers (A) represent at least 30%, advantageously at least 40%, and even more preferably at least 50%, of the total mass of the polymers (A), this total mass of the cyclodextrin units generally representing between 30 and 80%, and preferably between 40 and 60% of the total mass of the polymers (A).

Moreover the polymers (A) present in a composition generally have a mean molar mass by number of between 10 000 and 3 000 000 g/mole, advantageously between 20 000 and 2 000 000, and preferably between 100 000 and 1 500 000 g/mole. The polymers (A) preferably have the lowest possible polydispersity index (that is to say a ratio of the mean molar mass by weight to the mean molar mass by number), preferably less than 3, and even more advantageously less than 2.

The polysaccharide molecules (B) present in the particles of the compositions according to the invention include in a specific manner groups G which are capable of forming inclusion complexes with the cyclodextrin units of the polymers (A).

These groups G can in particular be linear or branched aliphatic groups having 8 to 18 carbon atoms. Advantageously they are linear alkyl groups having 8 to 18 carbon atoms. According to a particular variant, they may also be adamantyl groups.

Thus the macromolecules (B) present in the composition according to the invention are polysaccharides grafted by groups G as defined above. Preferably the groups G are aliphatic groups, and advantageously linear alkyl groups having 8 to 18 carbon atoms, or adamantyl groups, these groups being generally linked to the polysaccharide by way of an ester —COO-bond.

In a preferably manner, the grafted polysaccharides (B) are substituted polysaccharide derivatives, selected from amongst dextran, chitosan, amilose, amilopectin, hyaluronic acid, cellulose derivatives, starch, pullulan, pectin, alginates, heparin, carragheenans, fucan, curdlan, xylan, polyguluronic acid, xanthan, arabinan, polymannuronic acid, and their derivatives (such as for example dextran sulphate, amilose esters, or even cellulose acetate), these polysaccharides generally having a mean molar mass by mass between 5 000 and 2 000 000 g/mol, and preferably between 6 000 and 70 000. Advantageously, the macromolecules (B) are dextrans grafted preferably by linear alkyl groups comprising 8 to 18 carbon atoms or by adamantyl groups.

Substituted polysaccharides which are useful as molecules (B) according to the invention may be obtained for example by reaction of a polysaccharide and an acyl chloride ROCl (R designating an aliphatic chain as defined above) in proportions corresponding to the mean amount of aliphatic chains R which it wished to graft onto the polysaccharide. Preferably in this case the reaction of the polysaccharide of the acyl chloride ROCl takes place at a temperature of between 30 and 90° C. (typically at 80° C.) and advantageously in the presence of a base such as an amine, particularly of the pyridine type. An example of synthesis of this type is in particular described in an article by F. Arranz et al published in *Polymer*, vol. 29, pp 507-511 (1988).

The exact number and nature of the groups G present on the macromolecules (B) are preferably adapted to the nature of the polymer (A) used. In this connection it should in fact be emphasised that the compounds (A) and (B) must be chosen from amongst the associative systems which may, under certain concentration conditions, lead to an associative phase separation.

Thus when the polymer (A) comprises α-cyclodextrin units, it is generally preferable that the groups G present on the macromolecules (B) should be alkyl groups, preferably linear, having 6 to 18 carbon atoms, and preferably 8 to 10 carbon atoms.

When the polymer (A) comprises β-cyclodextrins, it is most often advantageous that the groups G present on the macromolecules (B) are alkyl groups, preferably linear, having 10 to 18 (preferably 12 to 16) carbon atoms, or adamantyl groups. If the polymer (A) contains only cyclodextrin units of the β-cyclodextrin type, it is particularly advantageous that the groups G are linear alkyls having 10 to 16 (preferably 12 to 16) carbon atoms, or adamantyl groups, these groups then preferably being linear alkyls having 12 carbon atoms or adamantyl groups.

In the case where the polymer (A) comprise γ-cyclodextrin units, it is generally preferable that the groups G present on the macromolecules (B) are alkyl groups, preferably linear, having 12 to 16 carbon atoms.

Moreover, the average number of groups G present on the macromolecules (B) is, characteristically, at least equal to 3 chains per macromolecule. As a general rule, this average number of groups G is all the greater as the size of the macromolecule is high and the number of cyclodextrin units in the compound (A) is substantial. It is most often advantageous that the average number of groups G present on the macromolecules (B) is at least equal to 5, and advantageously at least equal to 8. In general, the average number of groups G present on the macromolecules (B) remains less than or equal to 50, and advantageously less than or equal to 15.

As regards the grafted polysaccharide macromolecules, a "rate of grafting by the groups G" can be determined reflecting the quantity of groups G related to the size of the polysaccharide chain, that is to say to the number of saccharide units of the polysaccharide chain. This rate of grafting by the groups G is calculated on the basis of a NMR spectrum of the proton of the grafted polysaccharides, and it corresponds to the ratio of the integrations of the protons of the groups G, relative to the integrations of the protons of the polysaccharide skeleton. This rate is calculated according to the following formula:

rate of grafting by groups $G$ (%)=(integration of the signal corresponding to the protons of the groups $G$/number of protons on the groups $G$)/integration of the signal corresponding to the protons of the polysaccharide skeletons/number of protons on the polysaccharide skeletons)

The rate of grafting by the groups G of grafted polysaccharide macromolecules (B) is in general equal to 1%, and preferably at least equal to 2%. Advantageously this rate is greater than or equal to 3%.

However, in the more general case the number of groups G present on the macromolecules (B), most often hydrophobic, is limited by the fact that the compounds (B) must, characteristically, be water-soluble. It is equally desirable, as a general rule, to limit the number of groups G present on the macromolecules (B) in such a way as to avoid phenomena of auto-association between the macromolecules (B), more particularly when the groups G are hydrophobic groups of the aliphatic chain type. Because of this, the rate of grafting by the groups G is generally less than or equal to 8%, and preferably less than or equal to 6%. Thus it is typically between 3 and 4%.

In general, it is preferred that the macromolecules (B) have a mean molar mass by weight at least equal to 20 000 g/mole, preferably between 20 000 and 100 000 g/mole. It is preferred that the polymers (A) have a polydispersity index (that is to say a ratio of the mean molar mass by weight to the mean molar mass by number) as low as possible, preferably less than 3, and even more advantageously less than 2.

In a particularly preferred manner the compounds (A) and (B) present within the particles (p) of a composition according to the invention can be chosen from amongst the following associations:

Family 1: polymers (A) having from 18 to 1000, preferably from 100 to 600 β-cyclodextrin units/polysaccharides (B) of molecular mass between 6 000 and 70 000 (preferably dextrans) grafted by C12 aliphatic groups (preferably linear alkyl chains) and having a hydrophobic substitution rate of 3 to 5%, preferably less than 4%.

Family 2: polymers (A) having from 100 to 600, preferably from 200 to 500 β-cyclodextrin units/polysaccharides (B) of molecular mass between 6 000 and 70 000 (preferably dextrans) grafted by C10 aliphatic groups (preferably linear alkyl chains) and having a hydrophobic substitution rate of 5 to 7%.

Family 3: polymers (A) having from 18 to 1000, preferably from 100 to 600 β-cyclodextrin units/polysaccharides (B) of molecular mass between 6 000 and 70 000 (preferably dextrans) grafted by adamantyl groups and having a hydrophobic substitution rate of 3 to 4%.

Regardless of the exact nature of the compounds (A) and (B) used, it is generally preferred that within the particles (p) of a composition according to the invention the molar ratio of the total quantity of cyclodextrin units present within the polymers (A) relative to the total quantity of groups G present in the polysaccharide macromolecules (B) is between 1:3 and 3:1. This ratio is preferably at least equal to 0.7, and advantageously at least equal to 0.8. Furthermore, it is preferred that this ratio is less than or equal to 1.5, and advantageously less than or equal to 1.3. Typically this ratio may for example be between 0.9 and 1.1.

As a general rule, the concentration of compounds (A) and (B) within a composition according to the invention can vary to quite a large extent. However, most often the concentration of polymers (A) within the aqueous dispersion present in the composition according to the invention is between 0.01 and 10 g/l, advantageously between 0.02 and 2 g/l, and even more advantageously between 0.2 and 2 g/l. With regard to the concentration of macromolecules (B) within the aqueous dispersion, this is generally between 0.01 and 10 g/l, preferably between 0.08 and 9 g/l, and even more preferably between 0.8 and 8 g/l. Furthermore, it is generally preferred that the total concentration of polymers (A) and of modified macromolecules (B) within the aqueous dispersion is between 0.01 and 20 g/l.

In most cases, within a composition according to the invention the majority of the polymers (A) and of the macromolecules (B) is localised within the particles (p). Thus in general at least 80% by mass (preferably at least 85% by mass, and advantageously at least 90% by mass of the compounds (A) and (B) present in a composition according to the invention are contained in the particles (p).

According to another aspect, the present invention also relates to a method of preparing a composition as described previously. This method comprises a step (E), extremely simple to implement, which consists of effecting a mixture of an aqueous solution ($S_A$) comprising polymers (A) as defined previously and an aqueous solution ($S_B$) comprising polysaccharide macromolecules (B) as defined above, by choosing the volumes and the concentrations of the said solutions ($S_A$) and ($S_B$) in such a way as to obtain, after the mixing, an aqueous medium where the respective concentrations $C_A$ and $C_B$ in the said compounds (A) and (B) belong to the range for formation of a metastable dispersion for the auto-associative system (A+B) used.

Within the context of the present invention, the "range for formation of a metastable dispersion of an auto-associative system (A+B)" is understood to mean the range of concentrations of compounds (A) and (B) the existence of which was discovered by the inventors for the associations of type $a_{II}$, in which a direct mixture of compounds (A) and (B) as defined previously leads to the formation of a dispersion of particles of dimensions between 50 and 5000 nm. The term "range of concentrations" as used here designates a set of pairs ($C_A$; $C_B$). This term "range" refers to the ternary water/compound (A)/compound(B) diagrams which can be established for a system (A+B), by observing the system formed for the different water contents of water, compound (A) and compound (B). On such a ternary diagram the set of pairs ($C_A$; $C_B$) in which it is necessary to choose the respective concentrations of compounds (A) and (B) in the final medium in order to observe the formation of the metastable dispersion appears in effect in the form of a continuous zone, known as the "range of concentrations". In so far as the establishment of ternary diagrams for systems of type (A+B) is concerned, reference may be made in particular to the article "Macromolecular assemblies generated by inclusion complexes between amphiphatic polymers and b-cyclodextrin polymers in aqueous media" (C. Amiel et al, *ACS: Symposium Series*, No. 780, edited by C. McCormik "Stimuli-Responsive Water-Soluble and Amphiphatic Polymers", chapter 4 (2000).

In general, on a ternary water/compound(A)/compound(B) diagram of the aforementioned type, the range of formation of the metastable dispersion which has been discovered by the inventors is situated at the boundary between the ranges of formation of the two thermodynamically stable systems known from the prior art, namely the aforementioned systems of type (I) and (II).

In most cases, a composition according to the invention can be obtained from the majority of the associative systems of type (A+B) as defined previously if the medium obtained at the end of step (E) verifies the following two conditions:

the sum of the concentrations $C_A + C_B$ is between 0.1 and 10 g/l, and preferably between 1 g/l and 10 g/l; and the molar ratio of the total quantity of cyclodextrin units present within the polymers (A) introduced, relative to the total quantity of aliphatic chains present as substituents on the polysaccharide macromolecules (B) introduced, is between 1.3 and 3.1, and preferably between 1.2 and 2.1.

The solution ($S_A$) used in step (E) generally has a concentration between 0.01 g/l and 20 g/l, this concentration being advantageously between 0.1 and 10 g/l. The solution ($S_B$) for its part most often has a concentration between 0.01 g/l and 20 g/l, this concentration preferably being between 0.1 and 10 g/l.

As a general rule, and especially when the solutions ($S_A$) and ($S_B$) have the aforementioned concentrations, the ratio of the total volume of solution ($S_A$) introduced to the total volume of solution ($S_B$) introduced is most often between 1:9 and 9:1, and preferably this ratio by volume is between 1:5 and 5:1. In particular when the macromolecules (B) are grafted polysaccharides, of the modified dextran type, it is preferred that this ratio is between 1:5 and 1:1.25 and preferably between 1:3 and 1:0.75.

As a general rule, the method according to the present invention is extremely simple to implement. Thus, step (E) of the method according to the invention consists of a simple mixture, which is generally carried out at ambient temperature, that is to say most often between 15° C. and 30° C. Moreover, it should be noted that the method of preparation according to the invention can be limited merely to carrying out step (E).

Especially so as to produce the most homogeneous possible mixture of the solutions ($S_A$) and ($S_B$), it is often advantageous to carry out step (E) with agitation, but most of the time this agitation is not necessary in order to observe the formation of the metastable dispersion.

In a more general manner, the inventors have evidenced that, subject to being within the adapted range of concentrations and producing a direct mixture as quickly as possible of the solutions ($S_A$) and ($S_B$), the mixture of the said solutions leads spontaneously to the formation of the metastable dispersion.

In this connection, it should be emphasised that the method according to the invention does not necessitate the use of solvents or surfactants. For this reason a composition according to the invention is generally free from any trace of organic solvent or surfactant. Thus, according to a particular embodiment a composition according to the invention may comprise water and compounds (A) and (B) as defined previously, to the exclusion of any other compound.

Nevertheless, taking account of the presence of cyclodextrin units within their structure, the particles (p) present within a composition according to the invention are particularly adapted to produce the encapsulation of chemical compounds, and quite particularly to produce the encapsulation of chemical compounds having groups of a hydrophobic nature. The particular use of the compositions according to the invention for this purpose constitutes a particular object of the present invention.

The particles (p) present in the compositions according to the invention are able to integrate, in encapsulated form, numerous types of neutral or charged chemical compounds. The compounds capable of being encapsulated within the particles (p) of a composition according to the invention comprise in particular the compounds having hydrophobic groups, particularly alkyl groups, having in general 6 to 128 carbon atoms.

More specifically, the particles (p) present in a composition according to the invention are particularly well adapted to produce encapsulation of compounds capable of forming inclusion complexes with the cyclodextrin units which they comprise. For further details with regard to the formation of inclusion complexes between chemical compounds and cyclodextrins, as well as with regard to the nature of the compounds capable of forming such complexes, reference may be made to "Cyclodextrins and their inclusion complexes", Szejtli J., Academia Kiado, Budapest, 1982.

In general, simply placing the aforementioned chemical compounds in contact with a composition according to the invention is sufficient in order to produce the encapsulation of chemical compounds by the particles (p), in particular when the said composition is essentially based on water and particles (A) and (B).

In this scope, a composition according to the invention may for example be used as an absorbent composition, particularly for entrapping toxic agents or pollutants present in an aqueous medium, and in particular to eliminate compounds of the hydrocarbon type (particularly polycyclic aromatic hydrocarbons), halogenated aromatic compounds (such as chlorobenzene or chlorophenols), phthalic esters, or also iodine, particularly radioactive iodine, or pollutants of the pesticide type or textile dyes. In order to do this, it is generally sufficient to introduce the composition based on particles (p) within the medium to be purified. The particles (p) can, in this type of application, absorb (encapsulate) a quantity of compounds to be eliminated at least equal to 0.1 mole of compound per mole of cyclodextrins included in the particles, and may be up to 1 mole per mole of cyclodextrin, even up to 2 mole per mole of cyclodextrin, particularly for pollutants of the hydrocarbon type, particularly of the polycyclic aromatic hydrocarbon type.

The compositions according to the invention having chemical compounds encapsulated within their particles (p) may also be of interest in themselves. According to a particular aspect, the present invention also relates to such compositions according to the invention, where the particles (p) comprises at least one chemical compound (C), other than compounds (A) and (B).

In this type of composition, said compound (C) is in general a compound having groups of a hydrophobic nature, advantageously groups of the type having hydrocarbon chains having 8 to 18 carbon atoms, and preferably 10 to 18 carbon atoms. In an advantageous manner, this compound (C) is a compound capable of forming an inclusion complex with one of the cyclodextrin units contained in the polymers (A) present in the particles (p).

It is preferred that in a composition comprising a compound (C) of the aforementioned type the quantity of compound (C) integrated within the particles (p) represents at least 0.5% by mass relative to the total mass of the said particles (p). It is often advantageous in such a composition that the ratio by mass (C)/(A+B) of the total mass of the compounds (C) relative to the total mass of the compounds (A) and (B) is between 1% and 50%, this ratio being preferably greater than 2% and advantageously greater than 3%.

As already emphasised in the instant description, a composition according to the invention additionally comprising a compound (C) as defined above can in particular be obtained by simply placing the said compound (C) in contact with a composition according to the invention based on a preformed aqueous dispersion of particles (p) based on the compounds (A) and (B). In this context, it is naturally preferable that the particles (p) are essentially based on compounds (A) and (B), to the exclusion of the presence of any other compound, in particular of a compound capable of forming an inclusion complex with the cyclodextrin units present in the polymers (A). However, it is possible to envisage several successive steps for placing in contact with different types of compounds (C). The total quantity of compound (C) placed in contact with the composition in the course of this or these steps preferably represents between 4 and 100% by mass, and preferably between 10 and 80% by mass relative to the total mass of the particles (p) present initially in the composition. This quantity of compound (C) placed in contact with the composition advantageously represents between 10 and 70% by mass, and more preferably between 20 and 50% by mass relative to the total mass of the polymers (A).

In an advantageous manner, especially when it is desired to prepare a composition according to the invention additionally comprising compounds (C) capable of forming an inclusion complex with one of the cyclodextrin units contained in the polymers (A), the incorporation of the compounds (C) within the particles (p) may be achieved by using in the method of preparation according to the invention a solution ($S_A$) comprising in addition to the polymers (A) the compounds (C) which it is desired to integrate into the particles (p), this compound (C) advantageously forming inclusion complexes with cyclodextrin units present in the polymers (A). In this context, within the solution ($S_A$) the ratio by mass of compound (C)/polymer (A) is preferably between 10 and 100%, and more preferably between 20 and 50%. The presence of the compound (C) within the solution ($S_A$) does not generally modify the range of formation of the metastable dispersion for the auto-associative system (A+B) relative to the conditions to be implemented in the absence of the compound (C). For this reason, in the presence or absence of the compound (C) the volumes and the concentrations of the solutions ($S_A$) and ($S_B$) are chosen in such a way as to obtain, following the mixture, an aqueous medium where the respective concentrations $C_A$ and $C_B$ in the said compounds (A) and (B) belong to the range of formation of a metastable dispersion for the auto-associative system (A+B).

The exact nature of the compound (C) which may be encapsulated in a composition according to one of the aforementioned methods, can vary to quite a large extent. However, particularly in so far as the polymers (A) and the macromolecules (B) can be chosen from amongst non-toxic and biocompatible compounds and the presence of traces of organic solvents or surfactants can be avoided, one of the principal applications which can be envisaged for a composition according to the invention is the vectorisation of active substances, particularly of compounds having a therapeutic or cosmetic effect.

Thus, according to a particularly advantageous embodiment, a composition according to the invention may comprise by way of compound (C) within its particles (p) at least one active compound by way of medicament, this active compound (C) by way of medicament preferably being capable of forming an inclusion complex with one of the cyclodextrin units contained within the particles (p).

Such a composition according to the invention can be used in general by way of a pharmaceutical composition for administration by injection or orally, or also by the dermal or subcutaneous route, nasally, by the pulmonary route or by the ocular route and, more broadly, for any administration at the level of a mucous membrane, or at the level of a precise site (tumour, lumen of certain blood vessels, . . . ). In this context it is most often preferable that the composition is essentially constituted by water and compounds (A), (B) and (C), possibly in association with one or several pharmacologically acceptable excipients and adapted to the administration route envisaged. However, broadly the composition according to the invention can, in this type of application, take the form of any pharmaceutical formulation integrating an aqueous dispersion of the particles (p) comprising the active compound (C) by way of medicament. In the case of a composition specifically intended for administration by intravenous injection, it is generally preferred that the particles (p) integrating the compound (C) have a mean hydrodynamic diameter at least equal to 200 nm. With regard to the compositions intended for administration by intramuscular injection, it is preferred that the particles (p) having the compound (C) integrated in them have a mean hydrodynamic diameter between 200 and 5000 nm, preferably less than 1000 nm.

The compositions according to the invention, which have particles (p) based on grafted polysaccharides integrated in them by way of compounds (B), are of particular interest in terms of bioadhesion, which makes them extremely advantageous for application to the mucous membranes. For an application by the ocular route, it has proved particularly interesting that the compounds (B) present in the particles (p) are grafted hyaluronic acids.

The compositions according to the invention comprising an active compound (C) by way of medicament within their particles (p) generally induce, following their administration, a progressive release of the encapsulated compound (C), especially when the said compound (C) is a compound capable of forming an inclusion complex with one of the cyclodextrin units comprised in the particles (p), in particular when the said composition is administered in a patient intravenously. Thus with the aid of such a composition it is possible to achieve the prolonged administration of the active compound (C), in particular when this compound is chosen from amongst tamoxifen or its derivatives, or from amongst piroxicam and its derivatives. Numerous active substances are capable of being encapsulated in the particles (p) of the compositions according to the invention with the aim of prolonged salting out, and particular of the antiinfectious, antiinflammatory, antibacterial and antiparasitic agents, opioids, enzymes, or also polypeptides. Thus as active compounds (C) acting as a medicament which can be encapsulated in the particles (p), mention may be made in particular of molsidomine, ketoconazole, gliclazide, diclofenac, levonorgestrel, paclitaxel, hydrocortisone, pancratistatin, ketoprofen, diazepam, ibuprofen, nifedipin, testosterone, tamoxifen, furosemide, tolbutamide, chloramphenicol, benzodiazepines, naproxene, dexamethasone, diflunisal, anadamide, pilocarpine, daunorubicin, doxorubicin and diazepam.

In this context, without wishing to be associated in any way with a particular theory, it seems that it could be suggested that the release of the compound (C) is effected with a balance of distribution between the particles (p) and the external medium. Thus it seems that the internal hydrophobic cavity of each cyclodextrin constitutes a potential acceptor site for molecules of active substances or for lipophilic fragments thereof. The greater the affinity of the active substance for the cyclodextrins, the more its release will be slowed down. It has been possible in particular to demonstrate this concept with a model molecule, benzophenone, having a high affinity for cyclodextrins. Because of this, an active compound (C) acting as a medicament contained in the particles (p) of a composition according to the invention is most often released in a preferred manner at the level of the cells or the tissues where this compound is consumed, that is to say most often where it plays an effective therapeutic role.

As regards the compositions according to the invention comprising an active compound (C) acting as a medicament, it should be noted that the particles (p) can in general be administered as such by the oral route. In this case they can make it possible to achieve the oral administration of compound (C) with an unpleasant taste or smell (the encapsulation is generally capable of masking this taste or this smell) or of a compound (C) which is fragile and/or difficult to absorb orally, such as for example a compound chosen from amongst the antiinflammatories such as piroxicam, ibuprofen and ketoprofen, hypoglycaemic agents such as glicazide, contraceptive agents such as D-norgestrel, or also antifungal or antiparasitic agents such as ketoconazole or albendazole.

Moreover, without wishing to be associated in any way with a particular theory, it seems that it could be suggested that in so far as the compounds (B) are polysaccharides carrying groups G, the structure of the particles (p) is as a general rule such that the external layer of the particles (p) is essentially constituted by polysaccharides. In any case, in particular when the polysaccharides (B) are dextrans, the particles (p) generally have a tendency to adhere to the surface of certain mucous membranes, at the level of which they then deliver the active substance (C) which they contain, generally in a progressive manner. Thus by applying a composition according to the invention comprising a compound (C) with a therapeutic effect to a given (nasal, ocular, . . . ) mucous membrane it is possible to achieve a selective administration of the compound at the level of this mucous membrane. Moreover, it also seems that it could be suggested that, during oral administration, the specific structure of the particles (p) favours their translocation through the digestive epithelium, and their passage in the intact state into the blood system, where they can then allow prolonged release of the compound (C).

In the case where the particles (p) are intended for the vectorisation of compounds of the medicament type, it is generally advantageous that the compounds (A) and/or (B) are substituted by groups permitting cellular targeting. In this context it may be of interest for example that the compounds (A) and/or (B) are complexed by ligands of the folic acid type. The particles (p) then constitute specific so-called "third-generation" ligands.

Moreover, in such a way as to improve the "surreptitious" character of the particles (p) according to the invention (that is to say their capacity to circulate in a prolonged manner in the organism whilst avoiding detection by the immune system), it may be advantageous that the particles (p) according to the invention have external groups of the propylene glycol (PEG) type. In order to achieve this, use may be made by way of compounds (B) of polysaccharide molecules (preferably dextrans) carrying not only groups G as defined previously but also PEG chains. Another embodiment of particles grafted by PEG groups consists of adding to the system of compounds (A) and (B), in addition to the compounds (C), compounds of the PEG-[Alk] type, where Alk represents a $C_{10}$ to $C_{18}$ alkyl group, preferably a $C_{12}$ to $C_{16}$ alkyl group, or an admantyl group. If need be, as for the compounds (C), the addition of the compounds of the PEG-[Alk] type can be effected before or after formation of the particles from the associative system (A+B). However, it is generally preferred that this addition is effected after formation of the particles.

However, as a general rule, the presence of PEG groups is not necessary in order to ensure the surreptitious activity and, most often, the particles (p) prove capable of ensuring for example the vectorisation of the compounds with a reduced plasma half-life or with high toxicity, particularly at the level of the mononuclear phagocytes.

According to another embodiment, the compounds (C) which may be present within the particles (p) can also be cosmetic active substances, and the composition according to the invention can then be used advantageously by way of a cosmetic composition.

In this context the compounds (C) can for example be odorous compounds, for example of the terpene type, or a mixture of such compounds (perfumes, essences, . . . ). In such a composition the odorous compounds generally have a lower irritating power than in the non-encapsulated state, and they are released in a retarded manner, which improves the retention of the perfume. In the same way, other types of cosmetic agents preferably having a hydrophobic character may be immobilised as compound (C) within the particles (p) of a composition according to the invention, then released in a progressive manner. Thus a composition according to the invention may for example permit the controlled release of antiperspirant agents or also antibacterial agents. In a composition according to the invention intended for cosmetic use, the compound (C) may also be a colouring which is an irritant or has a certain toxicity, so that encapsulation thereof makes it possible to reduce the undesirable effects.

In a more general manner, the compositions according to the invention with the compounds (C) integrated in them can be used in order to achieve a progressive release of the said compounds (C) within a medium into which they are introduced or also in order to limit the contact between the compounds (C) and the said medium, for example with a view to protection of the compounds, when they are molecules which are fragile in relation to the medium under consideration, or also in order to isolate the compounds which may be pollutants (toxic agents, irritants, reagents, . . . ) for this medium. This general use of the compositions according to the invention comprising compounds (C) within the particles (p) constitutes another object of the present invention.

Whether or not they comprise a compound (C) by way of an addition, the compositions according to the invention can generally be subjected to a lyophilisation step, particularly when the composition is essentially constituted by an aqueous dispersion of the particles (p). If needed, this lyophilisation step is generally carried out by cooling the composition abruptly (generally in liquid air or liquid nitrogen), then sublimating the water under strong negative pressure. The compositions obtained at the end of such a lyophilisation step, which are generally present in the form of a compact powder of fluffy appearance, and which may be dispersed in the water in order to lead to the reconstitution of a dispersion of particles of the type of particles (p), constitute another particular object of the present invention.

The characteristics and advantages of the present invention will become even more apparent from the illustrative examples set out below.

The appended single drawing shows an enlarged view of particles according to the invention.

EXAMPLES

Example 1

Figure 1:
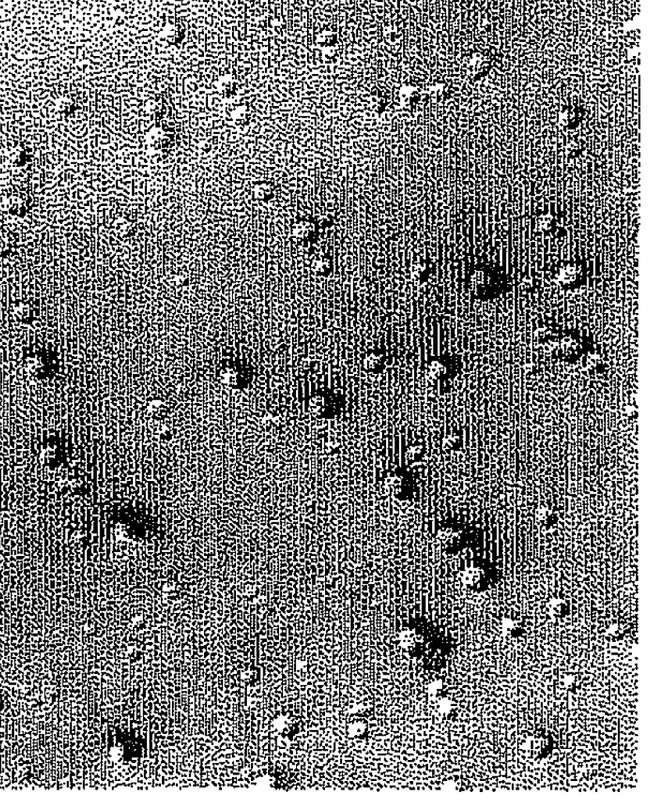

Synthesis of Polymers (A) Based on β-Cyclodextrin Units

Two polymers P1 and P2 were prepared based on cyclodextrins by reacting β-cyclodextrin (denoted by β-CD) with epichlorhydrin in a basic medium, using the mode of operation described in the *European Polymer Journal*, vol. 33, No. 1, pp 49-57 (1997).

1.1—Synthesis of Polymer P1

5 g of β-CD were dissolved in an aqueous solution of soda at 33% by mass in a two-necked flask. This mixture was left under agitation at ambient temperature (20° C.) for 24 hours in such a manner as to produce the deprotonation of the hydroxyl groups.

Then 2.7 ml of epichlorhydrin were introduced into the medium (molar ratio β-CD/epichlorhydrin=1/7) and the mixture was agitated vigorously and brought to 30° C. The medium was left under these conditions for 3 hours.

The reaction was then stopped by addition of acetone which dissolves the excess of epichlorhydrin. The supernatant acetone solution was then eliminated.

The polymer (precipitate) was dissolved in distilled water and the solution was brought to pH 12 and agitated for 24 hours. The pH value was then brought to 7 (by the addition of hydrochloric acid 6N), then the mixture was ultrafiltered through a membrane with a cut-off threshold of 1000 Dalton in order to eliminate the salts.

The polymer P1 obtained following these different steps was then lyophilised then stored in the freezer.

1.2—Synthesis of Polymer P2

As for polymer P1, 5 g of β-CD were dissolved in an aqueous solution of soda at 33% by mass in a two-necked flask. This mixture was left under agitation at ambient temperature (20° C.) for 24 hours in such a manner as to produce the deprotonation of the hydroxyl groups.

Then 3.8 ml of epichlorhydrin were introduced into the medium (molar ratio β-CD/epichlorhydrin=1/10) and the mixture was agitated vigorously and brought to 30° C. The medium was left to develop until it reached the immediate vicinity of gelation of the reaction medium, that is to say until a medium with high viscosity was obtained.

The reaction was then stopped by addition of acetone which dissolves the excess of epichlorhydrin. The supernatant acetone solution was then eliminated.

The polymer (precipitate) was dissolved in distilled water and the solution was brought to pH 12 and agitated for 24 hours. The pH value was then brought to 7 (by the addition of hydrochloric acid 6N), then the mixture was ultrafiltered through a membrane with a cut-off threshold of 1000 Dalton in order to eliminate the salts. A second ultrafiltration was then carried out through a membrane with a cut-off threshold of 100 000 Dalton in such a way as to eliminate the fractions of low molar mass.

The polymer P2 obtained following these different steps was then lyophilised then stored in the freezer.

The characteristics of the polymers P1 and P2 are set out in the table below (the molecular masses shown in this table are as measured by SEC chromatography, with pullulan calibration, and the average number of β-cyclodextrin units per copolymer was calculated from this molecular mass).

TABLE 1 characteristics of polymers P1 and P2

| Polymer (A) | M (g/mol) | Average number of β-cyclodextrin units per copolymer |
|---|---|---|
| P1 | 40 000 | 20 |
| P2 | 2 600 000 | 1350 |

Example 2

Synthesis of Dextrans Modified by Alkyl Chains (B)

Different dextrans modified by alkyl chains were prepared by reacting dextran and different acyl chlorides using the mode of operation described in Polymer, Vol. 29, pp 507-511 (1988).

More precisely, dextran of a molecular mass equal to 40 000 (dextran T40) was reacted with different alkyl chlorides (nature and quantity specified in Table 2 below) in the presence of pyridine (proton detector) and dimethylamino pyridine (DMAP) (catalyst).

In each of the syntheses effected, 4g of dextran were solubilised in 100 ml of previously distilled dimethylformamide in the presence of 1 g of lithium chloride LiCl. The reaction was carried out by adding to the medium obtained 0.5 g of DMAP, 0.031 ml of pyridine and alkyl chloride, and leaving it to react at 80° C. for 3 hours.

The polymer obtained was the purified by precipitation in isopropanol, then by dialysis after solubilisation in water. During this step the polymer was fractionated as a fuinction of its rate of modification by difference in solubility in water.

For this purpose, after solubilisation in water the solution was poured into a test tube and it was left to rest for 4 hours. Following this decantation, three fractions (upper, median and lower) of equal volumes were then separated. In each of the syntheses, one or several of these fractions (as indicated in Table 2 below) were dialysed with pure water through membranes with a cut-off threshold of 6000-8000 Dalton. Following the dialysis of the fraction under consideration, the modified dextran obtained was characterised by NMR in order to determine the rate of substitution by the alkyl chains, then it was lyophilised.

The characteristics of the modified dextrans DM1-DM5 thus prepared are set out in Table 2 below.

TABLE 2 characteristics of the modified dextrans DM1–DM5

| Modified dextran (B) | Nature of the grafted chains | Quantity of alkyl chloride used | Fraction taken following decantation | Rate of grafting |
|---|---|---|---|---|
| DM1 | linear $C_{12}$ alkyl chains | 0.5 ml | upper fraction | 5.8% |
| DM2 | linear $C_{10}$ alkyl chains | 0.4 ml | median fraction + lower fraction | 5.3% |
| DM3 | linear $C_{12}$ alkyl chains | 0.43 ml | upper fraction | 4.2% |
| DM4 | linear $C_{12}$ alkyl chains | 0.43 ml | median fraction | 3.3% |
| DM5 | adamantyl groups | 0.54 g | upper fraction | 3% |

Example 3

Preparation of Aqueous Dispersions of Particles According to the Invention

Different aqueous dispersions according to the invention were produced by mixing a volume V(A) of an aqueous solution of polymers (A) at a concentration C(A) with a volume V(B) of an aqueous solution of modified dextrans (B) at a concentration C(B). The conditions of the mixtures produced are set out below:

TABLE 3 conditions of mixtures

| Composition | Polymer (A) | Modified dextran (B) | C(A) | C(B) | V(A) | V(B) |
|---|---|---|---|---|---|---|
| C1 | P1 | DM1 | 10 mg/ml | 10 mg/ml | 1 ml | 1 ml |
| C2 | P1 | DM2 | 10 mg/ml | 10 mg/ml | 1 ml | 1 ml |
| C3 | P2 | DM3 | 0.6 mg/ml | 0.6 mg/ml | 1 ml | 1 ml |
| C4 | P2 | DM4 | 3 mg/ml | 3 mg/ml | 0.375 ml | 0.625 ml |
| C5 | P2 | DM5 | 2.5 mg/ml | 2.5 mg/ml | 1 ml | 1 ml |

The mean diameters of the particles observed in the dispersions C1 to C4 obtained immediately after the mixture and following 2 to 15 days of storage are set out in Table 4 below.

TABLE 4 evolution of the mean diameters of the particles present in the compositions C1 to C4

| Composition | Diameter of particles (t = 0) | Diameter of particles (t = 2 days) | Diameter of particles (t = 5 days) | Diameter of particles (t = 15 days) |
|---|---|---|---|---|
| C1 | 113 nm | 167 nm | 173 nm | 228 nm |
| C2 | 112 nm | — | 106 nm | — |
| C3 | 260 nm | 310 nm | — | — |
| C4 | 130 nm | 260 nm | 270 nm | 350 nm |
| C5 | 240 nm(*) | — | — | — |

(*)At the end of 1 day of storage, the mean diameter of the particles of the composition C5 is 330 nm.

Example 4

Influence of the Molar Mass of the Polymer (A)

The mixture was produced with 1 ml of a solution of modified dextran DM3 (10 mg/ml in water milliQ) with 1 ml of a solution of two polymers (A) of different molar masses (polymers P1 and P2 as defined in Example 1, of respective molecular masses 40 000 g/mole or 2 600 000 g/mole) equally at 10 mg/ml in water milliQ.

Table 5 below shows the evolution of the mean diameters of the particles obtained in the two cases:

TABLE 5 evolution of the mean diameters of the particles for two polymers (A) of different molar masses

| | Diameter (nm) | | | | |
|---|---|---|---|---|---|
| Polymer (A) | t = 0 | 3 days | 5 days | 7 days | 12 days |
| P1 M = 40 000 g/mole | 160 | 456 | 610 | gelation | gelation |

TABLE 5-continued evolution of the mean diameters of the particles for two polymers (A) of different molar masses

| Polymer (A) | Diameter (nm) | | | | |
|---|---|---|---|---|---|
| | t = 0 | 3 days | 5 days | 7 days | 12 days |
| P2 M = 2 600 000 g/mole | 198 | 230 | 261 | 255 | 275 |

Thus it will be noted that the particles obtained with a polymer (A) of low molecular mass are less stable than those obtained with a polymer (A) of higher molar mass (for P2 the diameter tends to stabilise after 5 days).

In the case of P1, however, it should be noted that the evolutions of diameter are less significant when the concentrations of the starting polymers are lower.

Example 5

Encapsulation of a Model Compound: Benzophenone

An aqueous solution of polymer P2 as defined in Example 1 (0.44 g/l) was produced, to which benzophenone was added with a molar ratio of benzophenone added: cyclodextrin equal to 1:1. This solution was left under agitation for 24 hours.

A composition of particles was prepared by mixture of 1 ml of the solution thus obtained with 1 ml of a solution of modified dextran DM3 as defined in Example 1 (0.44 g/l).

After mixture, the particles produced were ultracentrifuged (30 minutes at 40000 r.p.m. in a Beckman L7-55 centrifuge). The non-encapsulated benzophenone present in the supernatant was dosaged by spectrophotometry (absorption line at 261 nm).

The experiment was repeated using a molar ratio of benzophenone added: cyclodextrin equal to 1:3 for the solution of polymer P2.

The experiment was also repeated using modified dextran DM4 instead of DM3.

Finally, the experiment was also repeated using a molar ratio of benzophenone added cyclodextrin equal to 1:3 for the solution of polymer P2 and also replacing the modified dextran DM3 by DM4.

In the 4 cases, the yields of encapsulation of the benzophenone are between 30 and 40% (less than 70% of the benzophenone initially introduced is found in the supernatant).

With a molar ratio of benzophenone : cyclodextrin equal to 1:1 in the initial solution of P2, particles are produced comprising 1% by mass of benzophenone. With a molar ratio of benzophenone: cyclodextrin equal to 1:3, particles comprising 3% by mass of benzophenone are produced.

Example 6

Preparation of Compositions of Lyophilised Particles

Compositions of particles were prepared by mixture of two identical volumes (1 ml) of a solution of polymer (A) and a solution of modified dextran (B) under the conditions set out in Table 6 below.

The receptacles containing them were immersed in liquid air. The particles were then lyophilised (Christ LDC-1) for 24 hours, with or without the presence of cryoprotector (saccharose) as appropriate. It was demonstrated in this context that the use of glucose and maltose is a cryoprotector poorly adapted to this type of particles.

The lyophilisates obtained were then mixed with water milliQ in such a way as to reconstitute the compositions of particles.

The diameters before and after lyophilisation are set out in Table 6 below.

TABLE 6 tests of lyophilisation and demonstration of the redispersibility of the lyophilisates obtained

| Polymer solution | Modified dextran solution | Cryoprotector | Diameter (nm) | |
|---|---|---|---|---|
| | | | before lyophilisation | after lyophilisation |
| polymer P1 0.5 mol/l | dextran DM3 0.5 mol/l | no | 273 ± 64 | 157 ± 52 |
| polymer P2 1 mol/l | dextran DM3 1 mol/l | saccharose | 130 ± 50 | 178 ± 64 |
| polymer P2 1 mol/l | dextran DM1 1 mol/l | no | 116 ± 40 | 117 ± 47 |

Example 7

Stability of the Compositions According to the Invention Under Shear

A composition of particles according to the invention was prepared by mixture of 5 ml of solution of polymer P2 at 10 mg/ml in water milliQ and 5 ml of solution of modified dextran DM3 at 10 mg/ml in water milliQ. The mean diameter of the particles obtained is 178 nm.

6.3 ml of the composition of particles produced was subjected to shear in Godel cone geometry (DG41) on a Rhéo-Stress 100 flowmeter (Haake/Fisons). The study was carried out at 20° with a shear stress going from 0 to 2000 mPa in 300 seconds, maintained at 2000 mPa for 300 seconds, then decreased from 2000 to 0 mPa in 300 seconds.

Following this treatment, the final diameter of the particles was measured equal to 183 m. Thus, no significant evolution was noted.

The invention claimed is:

1. A composition comprising an aqueous dispersion of particles (p) of mean hydrodynamic diameter between 80 and 5000 nm, said particles comprising:
    (A) polymers comprising at least an average of four cyclodextrin units within their structure; and
    (B) macromolecules of polysaccharides comprising at least three aliphatic groups, said aliphatic groups capable of forming inclusion complexes with the cyclodextrins present in the structure of the polymers (A), wherein said compounds (A) and (B) are water-soluble in the isolated state, and
    said composition comprises compounds (A) and (B) dissolved in an aqueous medium comprising the aqueous dispersion of particles (p) wherein at least 80% by mass of the compounds (A and B) present in the composition are contained in the particles (p).

2. The composition of claim 1, wherein the particles (p) have a mean hydrodynamic diameter greater than or equal to 80 nm and less than or equal to 500 nm.

3. The composition of claim 1, wherein the polymers (A) have on average at least 9 cyclodextrin units within their structure.

4. The composition of claim 1, wherein the cyclodextrin units present in the polymers (A) comprise β-cyclodextrins.

5. The composition of claim 1, wherein the polymers (A) are obtained by polycondensation of cyclodextrin and epichlorhydrin molecules.

6. The composition of claim 1, wherein the polymers (A) have a mean molar mass by number of between 10 000 and 3 000 000 g/mole.

7. The composition of claim 1, wherein the aliphatic groups are linear or branched, having 8 to 18 carbon atoms.

8. The composition of claim 1, wherein a rate of grafting of the polysaccharides (B) by the aliphatic groups is between 1 and 8%.

9. The composition of claim 1, wherein particles (p) contain compounds (A) and (B) selected from the group consisting of:
   the polymers (A) having from 18 to 1000 β-cyclodextrin units/each of the polysaccharides (B) having a molecular mass between 6 000 and 70 000 grafted by $C_{12}$ aliphatic groups and having a hydrophobic substitution rate of 3 to 5%;
   the polymers (A) having from 100 to 600 β-cyclodextrin units/each of the polysaccharides (B) having a molecular mass between 6 000 and 70 000 grafted by $C_{10}$ aliphatic groups and having a hydrophobic substitution rate of 5 to 7%; and
   the polymers (A) having from 18 to 1000 β-cyclodextrin units/each of the polysaccharides (B) of molecular mass between 6 000 and 70 000 grafted by adamantyl groups and having a hydrophobic substitution rate of 3 to 4%.

10. The composition of claim 1, wherein the molar ratio of the total quantity of cyclodextrin units present within the polymers (A) relative to the total quantity of aliphatic chains present by way of substituents on the polysaccharide macromolecules (B) is between 1:3 and 3:1.

11. The composition of claim 1, wherein the particles (p) comprise at least one additional chemical compound (C) other than the compounds (A) and (B).

12. The composition of claim 11, wherein the compound (C) is a compound capable of forming an inclusion complex with one of the cyclodextrin units contained in the polymers (A) present in the particles (p).

13. The composition of claim 11, wherein a total mass of the particles (p) comprises at least 0.5% by mass the compound (C) integrated within the particles (p).

14. The composition of claim 11, wherein the compound (C) is a compound having a therapeutic or cosmetic effect and that the said composition is a pharmaceutical or cosmetic composition.

15. A method of preparation of the composition of claim 1, said method comprising a step (E) which comprises effecting a mixture of an aqueous solution ($S_A$) comprising polymers (A) as defined in claim 1 and an aqueous solution ($S_B$) comprising polysaccharide macromolecules (B) as defined in claim 1, volumes and concentrations of the solutions ($S_A$) and ($S_B$) being chosen in such a way as to obtain, after the mixing, an aqueous medium where respective concentrations $C_A$ and $C_B$ in the compounds (A) and (B) are in a range for forming a metastable dispersion for an auto-associative system (A+B) used.

16. The method of claim 15, wherein the medium obtained at the end of step (E):
   the sum of the concentrations $C_A + C_B$ is between 0.1 and 20 g/l; and
   the molar ratio of the total quantity of cyclodextrin units present within the polymers (A) introduced, relative to the total quantity of aliphatic chains present as substituents on the polysaccharide macromolecules (B) introduced is between 1:3 and 3:1.

17. The method of claim 15, wherein the concentration of the solution ($S_A$) is between 0.01 g/l and 20 g/l, the concentration of the solution ($S_B$) is between 0.01 g/l and 20 g/l, and the ratio of the total volume of solution ($S_A$) introduced to the total volume of solution ($S_B$) introduced is between 1:9 and 9:1.

18. A method of preparation of a composition of claim 11, which consists of placing the compound (C) in contact with a composition comprising an aqueous dispersion of particles (p) of mean hydrodynamic diameter between 80 and 5000 nm, wherein said particles comprises:
   (A) polymers comprising an average of at least four cyclodextrin units within their structure; and
   (B) macromolecules of polysaccharides comprising at least three aliphatic groups, said aliphatic groups capable of forming inclusion complexes with the cyclodextrins present in the structure of the polymers (A),
   wherein said compounds (A) and (B) are water-soluble in the isolated state, and said composition comprises compounds (A) and (B) dissolved in an aqueous medium comprising the aqueous dispersion of particles (p) wherein at least 80% by mass of the compounds (A and B) present in the composition are contained in the particles (p).

19. A method of preparation of a composition as claimed in claim 1 wherein the particles (p) comprise at least one additional chemical compound (C) other than the compounds (A) and (B), said method comprising effecting a mixture of an aqueous solution ($S_A$) comprising polymers (A) and the additional compound (C) and an aqueous solution ($S_B$) comprising modified polysaccharides (B), the volumes and the concentrations of the solutions ($S_A$) and ($S_B$) being chosen in such a way as to obtain, after mixing, an aqueous medium where respective concentrations $C_A$ and $C_B$ in the compounds (A) and (B) are in a range for forming a metastable dispersion for an auto-associative system (A+B) used.

20. A method comprising encapsulating chemical compounds by mixing the composition according to claim 1 with chemical compounds, thereby encapsulating the chemical compounds.

21. A method for progressive release of a compound comprising introducing the particles according to claim 11 into a medium, resulting in a progressive release of compounds (C) present within the particles (p) within a medium into which the composition is introduced, or in order to limit the contact between the compounds (C) and the medium.

22. A method for delivering the composition of claim 14, comprising delivering the composition containing compound (C), being an active compound by way of a medicament, of a pharmaceutical composition, to a mucous membrane, thereby resulting in the compound (C) being delivered in a progressive manner and/or to deliver this compound (C) in a selective manner to the mucous membrane.

23. A composition obtained by a lyophilisation of a composition according to claim 1.

24. The method of claim 16, wherein the polysaccharide macromolecules (B) introduced is between 1:2 and 2:1.

* * * * *